United States Patent [19]

Hirose et al.

[11] 4,139,632
[45] Feb. 13, 1979

[54] PSYCHOTROPIC 2-TRIFLUOROMETHYL-10-[3-(3-HYDROXY-PYRROLIDINO)-PROPYL]-PHENOTHIAZINE COMPOUNDS

[75] Inventors: Noriyasu Hirose, Kokubunji; Shizuo Kuriyama, Kami-Fukuoka, both of Japan

[73] Assignee: Eisai Co., Ltd., Tokyo, Japan

[21] Appl. No.: 714,322

[22] Filed: Aug. 13, 1976

[30] Foreign Application Priority Data

Aug. 29, 1975 [GB] United Kingdom ............... 35815/75

[51] Int. Cl.$^2$ .................... A61K 31/54; C07D 279/28
[52] U.S. Cl. ...................................... 424/247; 544/46
[58] Field of Search ................... 260/243 A; 424/247; 544/46

[56] References Cited

U.S. PATENT DOCUMENTS 3,004,028  10/1961  Dolliver et al. .................... 260/268
3,081,305  3/1963   Jacob et al. ....................... 260/243 A

FOREIGN PATENT DOCUMENTS 857547  12/1956  United Kingdom ............... 260/243 A
834370  5/1960   United Kingdom ............... 260/243 A Primary Examiner—Henry R. Jiles
Assistant Examiner—Bernard Dentz

[57] ABSTRACT

New phenothiazine derivatives having the general formula:

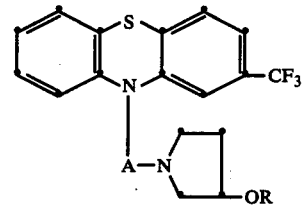

wherein R represents hydrogen atom or a lower alkyl group, and A represents a lower alkylene group, and process for the production thereof. The phenothiazine derivatives have remarkable activities against the central nervous system, and are useful as psychotropic drugs.

2 Claims, No Drawings

PSYCHOTROPIC 2-TRIFLUOROMETHYL-10-[3-(3-HYDROXY-PYR-ROLIDINO)-PROPYL]-PHENOTHIAZINE COMPOUNDS

The present invention relates to new phenothiazine derivatives, process for the production thereof, and therapeutial preparations containing such new phenothiazine derivatives. More particularly, the present invention relates to new and pharmacologically active phenothiazine derivatives having the general formula:

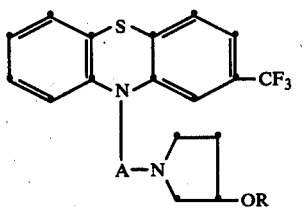

wherein R represents hydrogen atom or a lower alkyl group, and A represents a lower alkylene group, and pharmacologically acceptable acid addition salts thereof, and process for the production thereof, as well as therapeutical preparations thereof.

In the above formula (I), there may be mentioned, as a lower alkyl group R, for example, methyl, ethyl, propyl, isopropyl, butyl, iso-butyl and the like.

A lower alkylene group A includes a straight or branched alkylene group having 2 - 4 carbon atoms, such for example as ethylene, propylene, iso-propylene, 2-methyl-trimethylene, tetramethylene, and the like.

The expression of "pharmacologically acceptable acid addition salts" used in the present invention means non-toxic acid addition salts which were generally produced by reacting the free phenothiazine derivatives of the present invention with an organic acid or an inorganic acid. As these acid addition salts, there may be mentioned for example the corresponding hydrochloride, hydrobromide, sulphate, bisulfite, acetate, lactate, tartarate, succinate, p-toluene sulfonate, and the like.

The phenothiazine derivatives of the present invention represented by the general formula (I) may be produced by several synthetic routes, by taking the chemical structure of the derivatives (I) into consideration. Typical process for the production of the derivatives (I) comprises the reaction of the compound of the general formula:

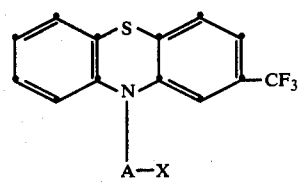

wherein X represents an acid residue of an active ester, and A has the same meanings as defined above, with a 3-substituted-pyrrolidine of the general formula:

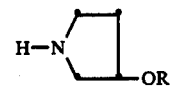

wherein R has the same meanings as defined above.

Illustrative acid residues of active esters in the general formula (II) include, for example, halogen such as chlorine, bromine, iodine and the like; $OSO_2H$; and an alkyl or an aryl sulfonyloxy such as methylsulfonyloxy, phenylsulfonyloxy, p-chlorophenyl-sulfonyloxy, and the like.

The reaction of the process of the present invention may be carried out with or without using a solvent. Such solvent can be properly selected from the group consisting of an aliphatic lower alcohol such as methanol, ethanol, propanol, iso-propanol, and the like; an aromatic hydrocarbon such as benzene, toluene, xylene, and the like; and a ketone such as methyl-isobutyl ketone, methyl-ethyl ketone and the like.

Generally speaking, it is preferable to use the solvent, whereby the reaction may be promoted and the after-treatment of the products may be facilitated.

When there are added in the reaction system a de-acid agent or a acid-removing agent such as sodium carbonate, potassium carbonate, pyridine, and the like, there are provided preferable results relating to the yields of the aimed products, the promotion of the reaction, and the like.

The reaction of the process of the present invention is carried out by using the equimolar amount of the compounds (II) and (III). Excess amount of the compound (III) can be substituted for the addition of the acid-removing agent.

The resulting compounds (I) can be readily converted by means of the conventional procedures into pharmacologically acceptable acid addition salts as mentioned above.

The compounds (I) of the present invention and their pharmacologically acceptable acid addition salts have the remarkable activities against the central nervous system, and are useful as psychotropic drugs.

This fact is proved by comparing 2-trifluoromethyl-10-[3-(3-hydroxy-pyrrolidino)-propyl]-phenothiazine hydrochloride, one of the compounds of the present invention (hereinafter referred to the compound A of the present invention), with 2-trifluoromethyl-10-(3-pyrrolidino-propyl)-phenothiazine hydrochloride, that is, the known homologue (refer to U.K. Pat. No. 857,547; hereinafter referred to the known compound (a), chloropromazine and fluphenazine, the latter two compounds being typical ones of the known phenothiazine series drugs, in relation to pharmacological activities such as psychotropic activity. The results for comparative measurement are shown in the following table.

TABLE

| Pharmacological activity | Compound A of the present invention | Known Compound a | Chlor-promazine | Flu-phen-azine |
|---|---|---|---|---|
| Inhibitory effect of spontaneous motor activity[1] | 3.3 | 3.8 | 13.0 | 2.1 |
| Anti-writhing Effect[2] | 1.0 | 4.1 | 9.4 | 2.5–10 |
| Anti-methan-phethamine[3] | 0.9 | 1.9 | 5.6 | 0.5 |
| Anti-tremorine activity[4] | 3.6 | 4.3 | 2.3 | 12.0 |
| $LD_{50}$ mg/Kg | | | | |

TABLE-continued

| Pharmacological activity | Compound A of the present invention | Known Compound a | Chlor- prom- azine | Flu- phen- azine |
|---|---|---|---|---|
| Oral Administration Subject (Test Animal) : | 1000≦ Mouse | 700≦ | 300≦ | 200≦ |

Numerical value means 50% effective amount (ED$_{50}$ mg/Kg) in oral administration.

Measurement of pharmacological activities are conducted in accordance with the procedures described in the following literatures:

| 1) | Svensson, T. H. et al | Psychopharmacologia (Berl.) 14, 157 (1969) |
| 2) | Siegmund, E. et al | Proc. Soc. EXP. Biol, & Med., 95. 729 (1957) |
| 3) | Piala, J. J. et al | J. Pharmacol. Exptl. Therap., 127, 55 (1959) |
| 4) | Everet, G. M. | Science, 124, 79 (1956) |

From the table, it is apparent that central nervous depressant activity of the compound A of the present invention is more intense than that of the known compound a. Especially, regarding anti-writing activity (analgetic activity) and anti-methanphethamine activity (neuroleptic activity), intensity of the compound A of the present invention is about 2–4 times, comparing with that of the known compound a. In the comparison of the compound A of the present invention with chlorpromazine, anti-tremorine activity of the compound A is almost equal to that of chlorpromazine, and it was recognized that there are remarkable differences wherein the other activities of the compound A are about 4 – 9 times more intense than those of chlorpromazine. Above all, there are superior neuroleptic activity and analgetic activity.

It is conventionally known that fluphenazine has the most intense central nervous depressant activity in the known phenothiazine series compounds. In comparison of the compound A of the present invention with such known fluphenazine, it was shown that although inhibitory effect of spontaneous motor activity and anti-methanphethamine activity of the compound A is about half of those of fluphenazine, anti-writhing activity and anti-tremorine activity (anti-Parkinson activity) are about 3 – 5 times intense than those of fluphenazine. For these reasons, the compound A of the present invention has central anticholinergic activity, and accordingly, there will be hardly occured extra pyramidal side-effect. Moreover, acute toxicity (LD$_{50}$) of the compound A is far less than that of chlorpromazine and fluphenazine.

As stated above, the compounds (I) of the present invention which are typically exemplified by the compound A and the pharmacologically acceptable acid addition salts thereof have an outstanding psychotropic activity and low toxicity. Therefore, these compounds can be used, as remarkable psychotropic drugs, for the treatment and prevention of schizophrenia, acute and chronic psychosis senile psychosis, neurosis, mania, depression, nausea, vomiting; and abatement of anxiety and apprehension.

The compounds of the present invention can be, as medicines, orally administered in the forms such for example as tablets, powders, capsules, granules, syrups and the like, or parenterally administered in the forms such as injections, suppositories, and the like.

For the adult, the active ingredient, that is, the compound of the present invention, is orally administered in an amount of about 10 – 300 mg/day, and particularly preferable amount is 40 – 150 mg/day.

Following Examples will serve to illustrate the invention, but should be construed that the invention is not restricted by these Examples.

EXAMPLE 1

Production of 2-trifluoromethyl-10-[3-(3-hydroxypyrrolidino)-propyl]-phenothiazine Fifty grams of 2-trifluoromethyl-10-(3-chloropropyl)-phenothiazine and 14 g of 3-hydroxy-pyrrolidine were dissolved in 400 ml of isopropanol. After 25 g of anhydrous sodium carbonate were added to the solution, said mixture was heated under reflux for 22 hours with stirring. Then, 1 g of potassium iodide was added to the mixture, and the whole was heated under reflux for another 5 hours. After cooling, the reaction mixture was filtered. The filtrate was distilled under vacuum. The resulting oily residues were dissolved in 500 ml of ethylether, and the solution was washed twice with aqueous saturated solution of sodium chloride, and dried on sodium sulfate. Removing the ethylether by distillation, a pale yellow viscous material was resulted. This material was dissolved in ethylacetate, and gaseous dry hydrogen chloride was introduced in said solution. White needle crystals deposited were collected by filtration, and recrystalized from acetoneacetic acid solution. The hydrochlorides of the object were obtained.

Yield 46.9 g (75.0% of theoretical value)

Melting point 146° C.

Value of mass spectrum (m/e) 394(M$^+$) : free base
Elementary analysis of the product having presumption formula $C_{20}H_{21}F_3N_2SO \cdot HCl$ gave the following:

|  | C | H | N |
|---|---|---|---|
| Calculated (%) | 55.74 | 5.16 | 6.50 |
| Found (%) | 56.00 | 5.31 | 6.79 |

EXAMPLE 2

Production of 2-trifluoromethyl-10-[3-(3-methoxypyrrolidino)-propyl]-phenothiazine According to the procedure of the preceding example 1, 50 g of 2-trifluoromethyl-10-(3-chloropropyl)-phenothiazine and 16 g of 3-methoxy-pyrrolidine were treated. White needle crystals of hydrochlorides of the objects were obtained.

Yield 49.2 g (76.2% of theoretical value)

Melting point 120° C – 121° C.

Value of mass spectrum (m/e) 408(M$^+$) : free base
Elementary analysis of the product having presumptive formula $C_{21}H_{23}F_3N_2SO \cdot HCl$ gave the following:

|  | C | H | N |
|---|---|---|---|
| Calculated (%) | 56.68 | 5.45 | 6.30 |
| Found (%) | 56.59 | 5.58 | 6.59 |

EXAMPLE 3

Production of 2-trifluoromethyl-10-[3-(3-ethoxypyrrolidino)-propyl]-phenothiazine According to the procedure of the preceeding example 1, 50 g of 2-trifluoromethyl-10-(3-chloropropyl)-phenothiazine and 17.5 of 3-ethoxy-pyrrolidine were treated. White needle crystals of hydrochlorides of the object were obtained.

Yield 45.6 g (68.4% of theoretical value)
Melting point 125° C – 127° C
Value of mass spectrum (m/e) 422 (M$^+$) : free base
Elementary analysis of the product having presumptive formula $C_{22}H_{25}F_3N_2SO \cdot HCl$ gave the following:

|  | C | H | N |
|---|---|---|---|
| Calculated (%) | 57.57 | 5.72 | 6.11 |
| Found (%) | 57.42 | 5.91 | 5.84 |

EXAMPLE 4

Preparation of tablets

| Formulation: | |
|---|---|
| 2-Trifluoromethyl-10-[3-(3-hydroxy-pyrrolidino)-propyl]-phenothiazine hydrochloride | 10.0g |
| Crystalline cellulose | 24.0g |
| Corn starch powder | 12.0g |
| Lactose | 53.7g |
| Calcium stearate | 0.3g |
| | 100.0g |

Using this formulation, 1000 tablets containing 10 mg of the active ingredient for each tablet were prepared by means of the conventional procedures.

EXAMPLE 5

Preparation of granule

| Formulation: | |
|---|---|
| 2-Trifluoromethyl-10-[3-(3-hydroxy-pyrrolidino)-propyl]-phenothiazine hydrochloride | 50.0g |
| Mannitol | 200.0g |
| Lactose | 720.0g |
| Hydroxypropyl cellulose | 30.0g |
| | 1000.0g |

Using this formulation, 1000g. of granule containing 5% of the active ingredient were prepared by means of the conventional procedures.

EXAMPLE 6

Preparation of capsules

| Formulation: | |
|---|---|
| 2-Trifluoromethyl-10-[3-(3-hydroxy-pyrrolidino)-propyl]-phenothiazine hydrochloride | 10.0g |
| Crystalline cellulose | 60.0g |
| Corn starch powder | 25.0g |
| Talc | 5.0g |
| | 100.0g |

Using this formulation, 1000 capsules containing 10 mg of the active ingredient for each capsule were prepared by means of the conventional procedures. Capsule No. 4 defined by the Japanese Pharmacopoeia was used.

EXAMPLE 7

Preparation of syrup

| Formulation: | |
|---|---|
| 2-Trifluoromethyl-10-[3-(3-hydroxy-pyrrolidino)-propyl]-phenothiazine hydrochloride | 50.0g |
| Sorbitol | 200.0g |
| Sucrose | 100.0g |
| Methylparaben | 2.0g |
| Propylparaben | 1.0g |
| Orange essence | 1.0g |
| Distilled water amounting to | 1000.0 ml |

Using this formulation, 1000 ml of syrup containing 5% of the active ingredient were prepared by means of the conventional procedures.

EXAMPLE 8

Preparation for ampoules for injection

| Formulation: | |
|---|---|
| 2-Trifluoromethyl-10-[3-(3-hydroxy-pyrrolidino)-propyl]-phenothiazine hydrochloride | 10.0g |
| Sodium chloride | 9.0g |
| Distilled water amounting to | 1000.0 ml |

Using this formulation, 1000 ampoules for injection containing 1% of the active ingredient were prepared by means of the conventional procedures, the respective contents of the ampoules being 1 ml of the solution.

What is claimed is:

1. A member selected from the group consisting of 2-trifluoromethyl-10-[3-(3-hydroxy-pyrrolidino)-propyl]-phenothiazine and a pharmacologically acceptable acid addition salt thereof.

2. A psychotropic composition which comprises a psychotropically acceptable amount of a member selected from the group consisting of 2-trifluoromethyl-10-[3-(3-hydroxypyrrolidino)-propyl]-phenothiazine and a pharmacologically acceptable acid addition salt thereof in admixture with a pharmaceutically acceptable carrier therefor.

* * * * *